(12) United States Patent
Ido et al.

(10) Patent No.: US 8,192,050 B2
(45) Date of Patent: Jun. 5, 2012

(54) ILLUMINATION DEVICE FOR VISUAL INSPECTION AND VISUAL INSPECTION APPARATUS

(75) Inventors: Katsuya Ido, Gifu (JP); Takayoshi Tsuiki, Gifu (JP); Masayuki Ohta, Tokyo (JP)

(73) Assignee: Sony Corporation, Tokyo (JP)

( * ) Notice: Subject to any disclaimer, the term of this patent is extended or adjusted under 35 U.S.C. 154(b) by 257 days.

(21) Appl. No.: 12/729,452

(22) Filed: Mar. 23, 2010

(65) Prior Publication Data
US 2010/0246174 A1 Sep. 30, 2010

(30) Foreign Application Priority Data

Mar. 31, 2009 (JP) ................................. 2009-085257

(51) Int. Cl.
*F21S 4/00* (2006.01)
*F21V 21/00* (2006.01)
(52) U.S. Cl. ............... 362/249.02; 362/247; 362/311.02; 362/327; 362/350; 362/800
(58) Field of Classification Search .......... 362/230–231, 362/235–238, 240–247, 249.01–249.02, 362/296.01, 307–309, 311.02, 326–327, 362/350, 800
See application file for complete search history.

(56) References Cited

FOREIGN PATENT DOCUMENTS

| JP | 58-070150 | 4/1983 |
|---|---|---|
| JP | 05-288527 | 11/1993 |
| JP | 10-170450 | 6/1998 |
| JP | 2000-193432 | 7/2000 |
| JP | 2001-245323 | 9/2001 |
| JP | 2004-509325 | 3/2004 |
| JP | 2005-017234 | 1/2005 |

*Primary Examiner* — Jason Moon Han
(74) *Attorney, Agent, or Firm* — Wolf, Greenfield & Sacks, P.C.

(57) ABSTRACT

An illumination device for visual inspection includes: a transmissive reflector plate that is formed of a light transmitting material, has an opening in a center, assumes a dome shape, a radius of which is gradually expanded downward with a center axis of the opening set as a center, and has a lower surface formed of a reflecting surface on which fine unevenness for diffusing and reflecting light from below is formed and an upper surface located on an opposite side of the lower surface; first, second, and third light source units that irradiate light on an inspection object, the first, second, and third light source units being provided on the upper surface of the transmissive reflector plate and arranged in a place below the opening and passing the center axis; and a fourth light source unit that irradiates light on the inspection object and being provided below the transmissive reflector plate.

8 Claims, 6 Drawing Sheets

ILLUMINATION DEVICE FOR VISUAL INSPECTION AND VISUAL INSPECTION APPARATUS

BACKGROUND OF THE INVENTION

1. Field of the Invention

The present invention relates to an illumination device for visual inspection and a visual inspection apparatus.

2. Description of the Related Art

Various visual inspection apparatuses are proposed that image inspection objects with imaging apparatuses and inspect the inspection objects on the basis of obtained images. The visual inspection apparatuses are provided with an illumination device for visual inspection that irradiate illumination light on the inspection subjects.

As one of such visual inspection apparatuses, a visual inspection apparatus employing a so-called optical cutting method is proposed that projects a laser beam on an inspection object while scanning the laser beam on the inspection object with an illumination device for visual inspection to perform imaging and obtains a three-dimensional image of the inspection object on the basis of obtained image data (see JP-A-2000-193432).

However, when the optical cutting method is used, there is a drawback in that the visual inspection apparatus is large because the illumination device for visual inspection projects the laser beam while scanning the laser beam.

Therefore, it is conceivable to use a photometric stereo method (see JP-A-2001-245323) for obtaining three-dimensional data of an inspection object from plural image data obtained by changing an irradiation direction of a light source with respect to the inspection object.

This is because, in the photometric stereo method, the irradiation direction of the light source with respect to the inspection object only has to be changed by switching plural light sources and the configuration of an illumination device for visual inspection is simplified compared with the illumination device for visual inspection that scans the laser beam.

An illumination device for visual inspection for performing visual inspection using the photometric stereo method is proposed (see JP-A-2005-17234).

When the visual inspection of the inspection object is performed in this way, an illumination device for visual inspection having a different configuration is necessary according to a method for obtaining an image.

SUMMARY OF THE INVENTION

Concerning an inspection object for which strict accuracy management is requested such as cream solder printed on an electronic circuit board and an electronic component mounted on an electric circuit board, it is not sufficient to perform only visual inspection based on a three-dimensional image. It is demanded to perform visual inspection based on a two-dimensional image together with the visual inspection based on three-dimensional image.

However, in the past, in order to carry out the visual inspection based on a three-dimensional image and a two-dimensional image, an illumination device for visual inspection for a three-dimensional image and an illumination device for visual inspection for a two-dimensional image have to be separately prepared.

Therefore, there is a disadvantage in reducing labor and time and equipment cost necessary for inspection.

Thus, it is desirable to provide an illumination device for visual inspection and a visual inspection apparatus that are advantageous in reducing labor and time and cost necessary for visual inspection while coping with plural kinds of visual inspection performed by using a three-dimensional image and a two-dimensional image.

According to an embodiment of the present invention, there is provided an illumination device for visual inspection including: a transmissive reflector plate that is formed of a light transmitting material, has an opening in the center, assumes a dome shape, a radius of which is gradually expanded downward with a center axis of the opening set as the center, and has a lower surface formed of a reflecting surface on which fine unevenness for diffusing and reflecting light from below is formed and an upper surface located on the opposite side of the lower surface; first, second, and third light source units that irradiate light on an inspection object, the first, second, and third light source units being provided on the upper surface of the transmissive reflector plate and arranged in a place below the opening and passing the center axis; and a fourth light source unit that irradiates light on the inspection object, the fourth light source unit being provided below the transmissive reflector plate, wherein the first light source unit includes plural light sources arranged in an first annular area on the upper surface with the center axis set as the center, lights emitted from the plural light sources being transmitted through the transmissive reflector plate and crossing an imaginary plane, which is orthogonal to the center axis and passes through the inspection object, at a first angle to illuminate the inspection object, the second light source unit includes plural light sources arranged in a second annular area on the upper surface having a radius larger than that of the first annular area with the center axis set as the center, lights emitted from the plural light sources being transmitted through the transmissive reflector plate and crossing the imaginary plane at a second angle smaller than the first angle to illuminate the inspection object, the third light source unit includes plural light sources arranged in a third annular area on the upper surface located between the first annular area and the second annular area with the center axis set as the center, lights emitted from the plural light sources being transmitted through the transmissive reflector plate and crossing the imaginary plane at a third angle between the first angle and the second angle to illuminate the inspection object, and the fourth light source unit includes plural light sources arranged along a lower part of the outer circumference of the transmissive reflector plate, lights emitted from the plural light sources being diffused and reflected by the lower surface of the transmissive reflector plate to illuminate the inspection object.

According to another embodiment of the present invention, there is provided a visual inspection apparatus including: a base including a base body on which an inspection object is placed and a column erected from the base body; an imaging apparatus supported by the column with an optical axis of an imaging optical system thereof directed downward; a transmissive reflector plate that is supported by the column and formed of a light transmitting material, has an opening in the center through which the imaging apparatus is inserted from above, assumes a dome shape, a radius of which is gradually expanded downward with a center axis of the opening set as the center, and has a lower surface formed of a reflecting surface on which fine unevenness for diffusing and reflecting light from below is formed and an upper surface located on the opposite side of the lower surface; first, second, and third light source units that irradiate light on an inspection object, the first, second, and third light source units being provided on the upper surface of the transmissive reflector plate and arranged in a place below the opening and passing the center axis; and a fourth light source unit that irradiates light on the inspection object, the fourth light source being provided below the transmissive reflector plate, wherein the first light source unit includes plural light sources arranged in an first annular area on the upper surface with the center axis set as the center, lights emitted from the plural light sources being transmitted through the transmissive reflector plate and crossing an imaginary plane, which is orthogonal to the center axis and passes through the inspection object, at a first angle to illuminate the inspection object, the second light source unit includes plural light sources arranged in a second annular area on the upper surface having a radius larger than that of the first annular area with the center axis set as the center, lights emitted from the plural light sources being transmitted through the transmissive reflector plate and crossing the imaginary plane at a second angle smaller than the first angle to illuminate the inspection object, the third light source unit includes plural light sources arranged in a third annular area on the upper surface located between the first annular area and the second annular area with the center axis set as the center, lights emitted from the plural light sources being transmitted through the transmissive reflector plate and crossing the imaginary plane at a third angle between the first angle and the second angle to illuminate the inspection object, and the fourth light source unit includes plural light sources arranged along a lower part of the outer circumference of the transmissive reflector plate, lights emitted from the plural light sources being diffused and reflected by the lower surface of the transmissive reflector plate to illuminate the inspection object.

According to the embodiments, since the first, second, third, and fourth light source units are selected and used, it is possible to cope with plural kinds of visual inspection performed by using a three-dimensional image and a two-dimensional image. Therefore, the illumination device for visual inspection and the visual inspection apparatus are advantageous in reducing labor and time and cost necessary for visual inspection.

DESCRIPTION OF THE PREFERRED EMBODIMENTS

An embodiment of the present invention is explained below with reference to FIGS. 1 to 6.

First, an illumination device for visual inspection and a visual inspection apparatus according to the embodiment are explained.

Figure 4:
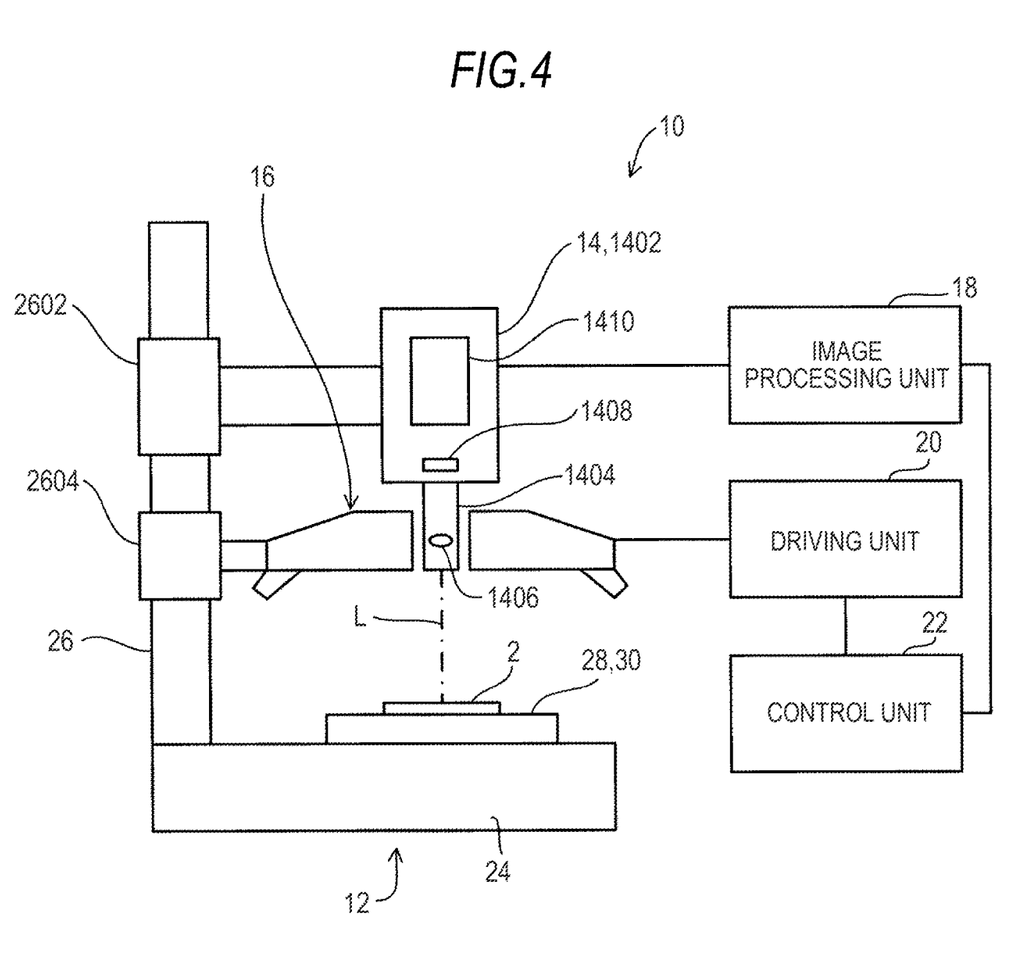
FIG. 4 is a diagram of the configuration of the illumination device for visual inspection 16 and a visual inspection apparatus 10 according to the embodiment.

As shown in FIG. 4, a visual inspection apparatus 10 includes a base 12, an imaging apparatus 14, an illumination device for visual inspection 16 according to the embodiment, an image processing unit 18, a driving unit 20, a control unit 22 and the like.

The base 12 includes a tabular base body 24 and a column 26 erected on a rear section of the base body 24.

An XY table 28 movable in two directions orthogonal to each other in the horizontal plane with respect to the base body 24 is provided on the upper surface of the base body 24.

The upper surface of the XY table 28 is formed as a flat placing surface 30. An inspection object 2 is placed on the placing surface 30.

An imaging-apparatus attaching section 2602 is coupled to an upper portion of the column 26 to be adjustable in position in an up to down direction.

An illumination-device-for-visual-inspection attaching section 2604 is coupled to a middle portion of the column 26 to be adjustable in position in the up to down direction.

The imaging apparatus 14 includes a rectangular parallelepiped body 1402 and a cylindrical lens barrel 1404 projected from the front surface of the body 1402.

The lens barrel 1404 houses and holds an imaging optical system 1406 that takes a subject image.

The body 1402 houses an imaging element 1408 that images the subject image focused by the imaging optical system 1406 and a signal processing unit 1410 that generates a video signal on the basis of an imaging signal generated by the imaging element 1408.

A side of the body 1402 is attached to the imaging-apparatus attaching section 2602, whereby the imaging apparatus 14 is supported on the base 12 with an optical axis L of the imaging optical system 1406 directed downward. The imaging apparatus 14 in this supported state is located in a place spaced apart above the placing surface 30. The optical axis L of the imaging optical system 1406 is orthogonal to the placing surface 30.

Therefore, when an image of the inspection object 2 placed on the placing surface 30 is focused on the imaging element 1408 by the imaging optical system 1406, the imaging element 1408 supplies an imaging signal to the signal processing unit 1410. The signal processing unit 1410 generates a video signal that indicates the image of the inspection object 2.

The image processing unit 18 applies, on the basis of the control by the control unit 22, image processing based on various publicly-known methods in the past to the video signal supplied from the signal processing unit 1410 to thereby generate three-dimensional image data and two-dimensional image data of the inspection object 2.

The driving unit 20 controls, on the basis of the control by the control unit 22, supply of a driving current to a light source of the illumination device for visual inspection 16.

The control unit 22 determines, on the basis of the three-dimensional image data and the two-dimensional image data supplied from the image processing unit 18, the quality of the inspection object 2 according to whether the inspection object 2 satisfies conditions set in advance. The control unit 22 supplies a result of the determination to a not-shown external apparatus.

The external apparatus is, for example, a display apparatus that displays the quality on the basis of the determination result or a conveying apparatus that classifies the inspection object 2 into a non-defective product or a defective product on the basis of the determination result.

The inspection object 2 is explained below.

Figure 2:
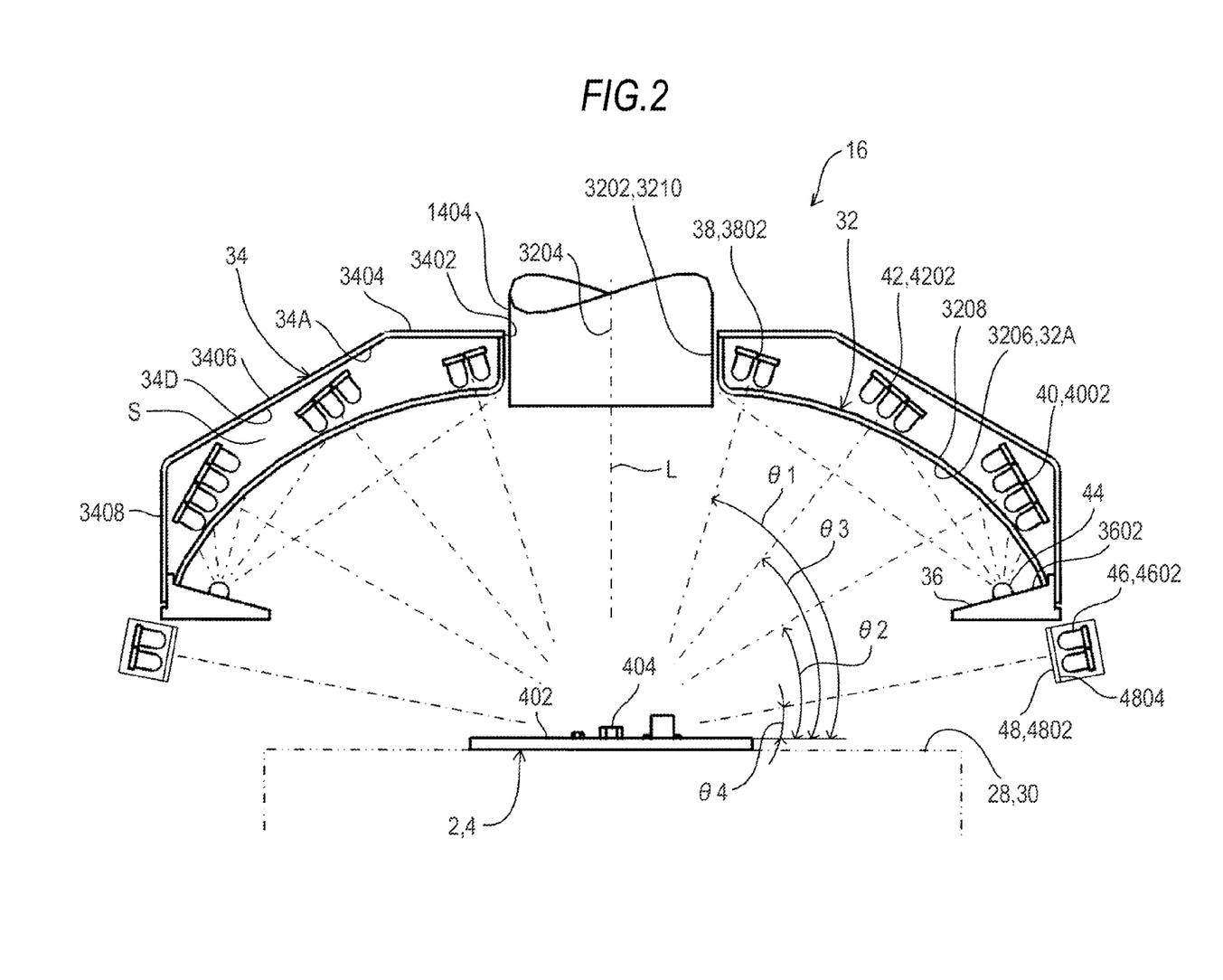
FIG. 2 is a sectional view of the configuration of the illumination device for visual inspection 16 according to the embodiment.
Figure 5:
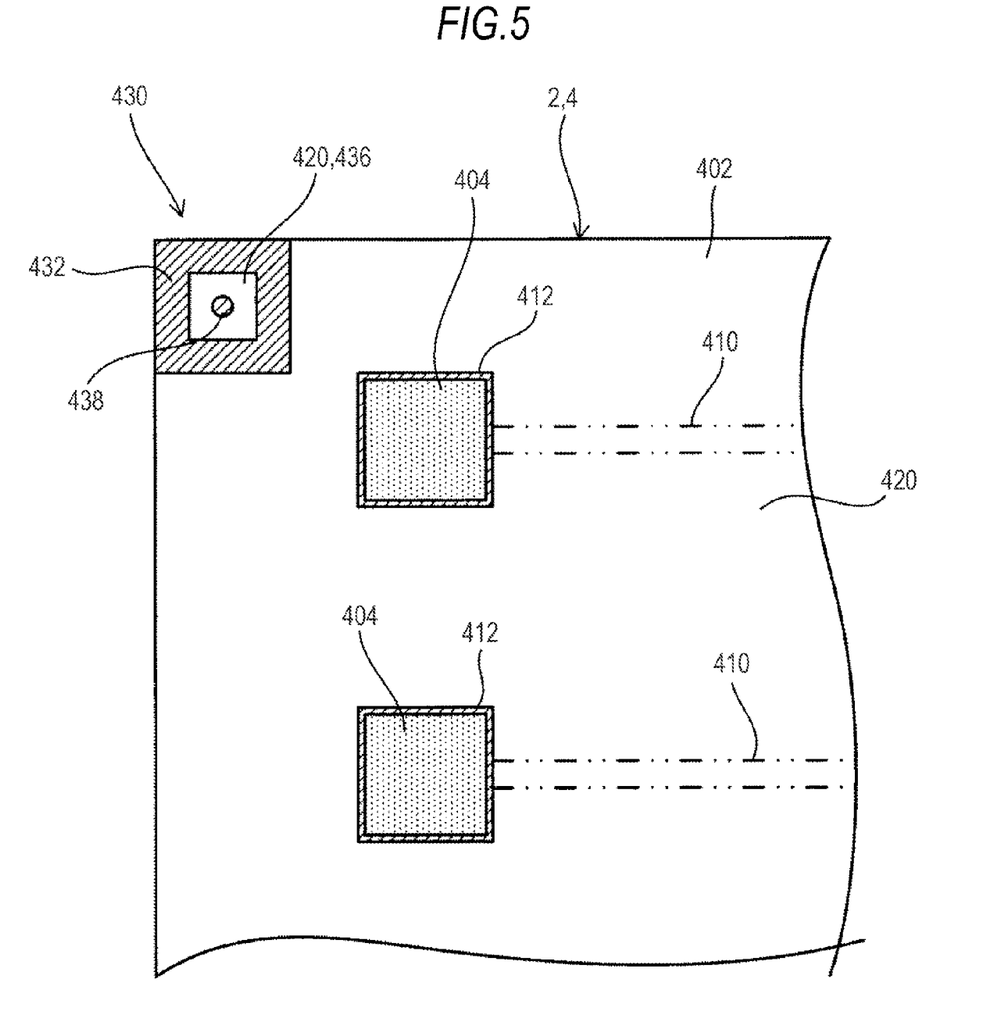
FIG. 5 is a plan view of a state in which cream solder 404 are printed on a printed wiring board 402.

In this embodiment, as shown in FIGS. 2 and 5, the inspection object 2 is an electronic circuit board 4.

In the following explanation, it is assumed that, as the electronic circuit board 4, a printed wiring board 402 applied with cream solder 404 by printing as shown in FIG. 5 is visually inspected.

Alternatively, it is assumed that the printed wiring board 402 applied with the cream solder 404 mounted with a chip component 406 as shown in FIG. 2 is visually inspected.

As shown in FIG. 5, in most cases, wiring patterns 410 made of copper foil and pads 412 made of copper foil used for soldering are formed on the surface of the printed wiring board 402.

A section excluding the pads 412 on the surface of the printed wiring board 402 is covered with a resist 420 made of an insulating material.

Plural positioning marks 430 indicating reference positions for the wiring patterns 410 and the pads 412 are formed on the surface of the printed wiring board 402.

Each of the positioning marks 430 are formed as explained below.

The wiring patterns 410 and the pads 412 are formed by copper foil 432 on the printed wiring board 402. The copper foil 432 is left in a place where the positioning mark 430 is formed. In a process for forming the resist 420, a rectangular resist section 436 made of a resist is formed on the inner side of an area of the remaining copper foil 432. When the rectangular resist section 436 is formed, a circular hole 434 for exposing the copper foil 432 is formed in the center of the rectangular resist section 436.

Consequently, the rectangular resist section 436 and a circular copper foil section 438 in the center of the resist section 436 are formed. The positioning mark 430 is formed by the resist section 436 and the copper foil section 438.

The illumination device for visual inspection 16 according to this embodiment is explained.

Figure 1:
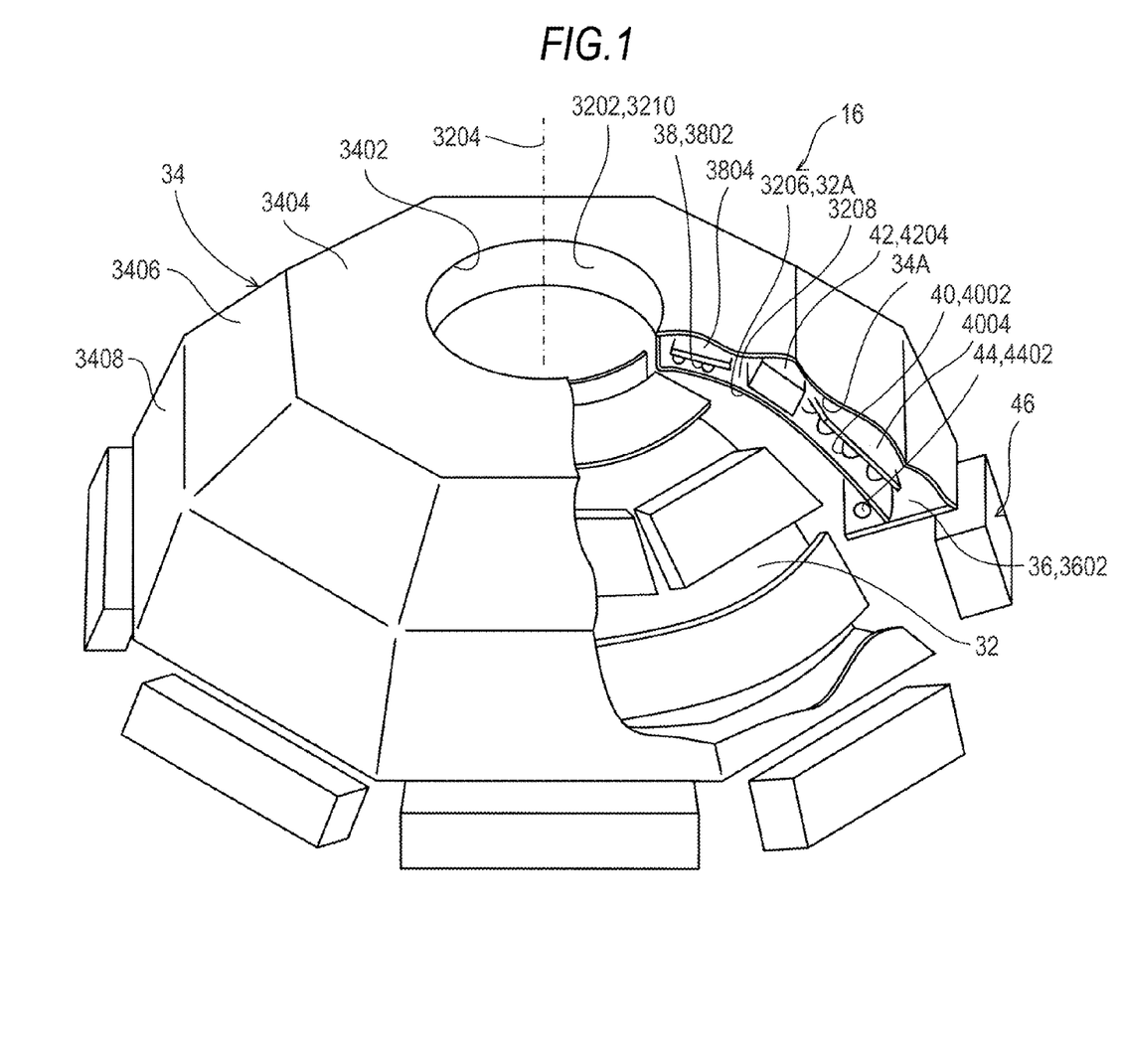
FIG. 1 is a partially cutaway perspective view of the configuration of an illumination device for visual inspection 16 according to an embodiment of the present invention.
Figure 3:
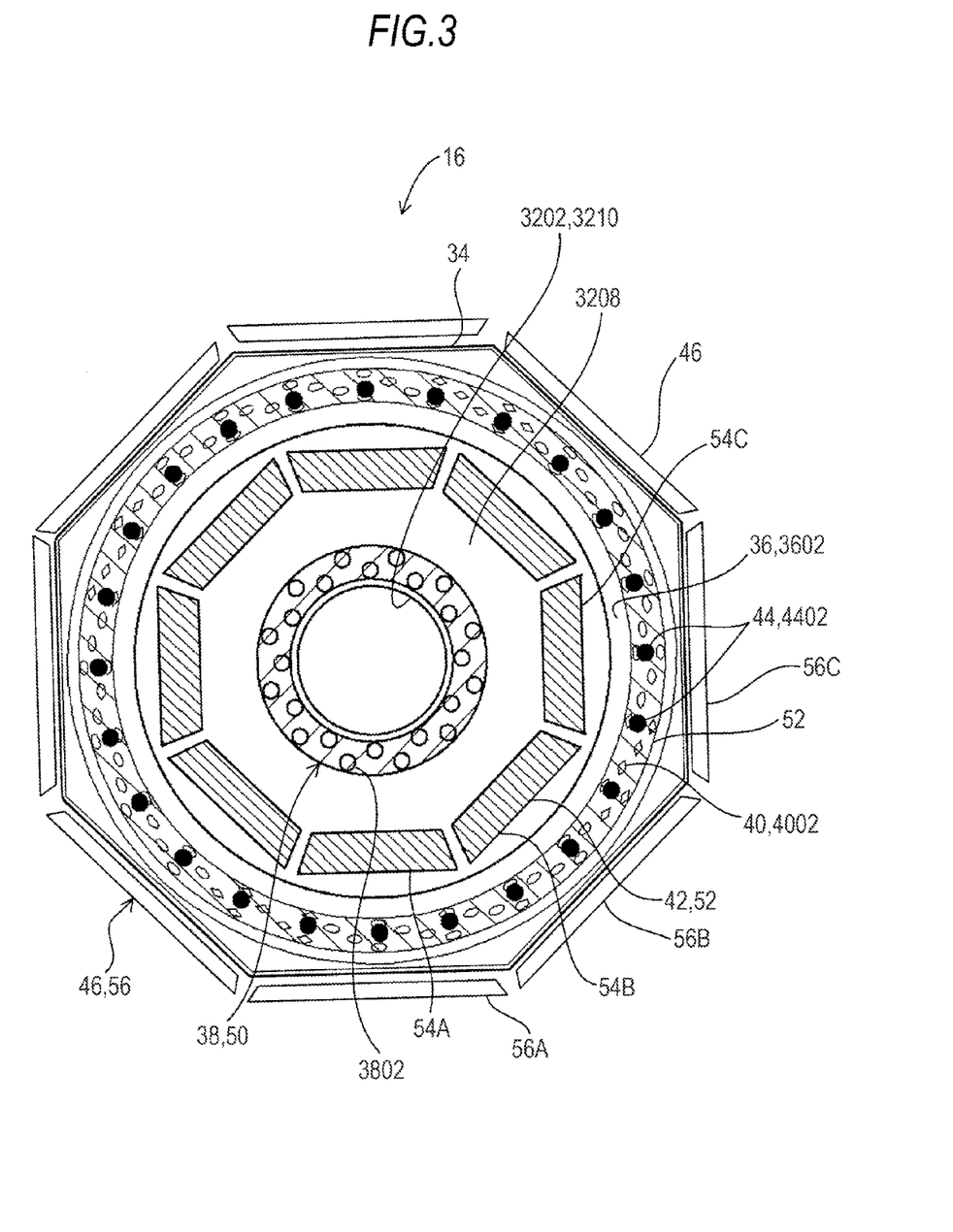
FIG. 3 is a plan view of the configuration of the illumination device for visual inspection 16 according to the embodiment.

As shown in FIGS. 1 to 3, the illumination device for visual inspection 16 includes a transmissive reflector plate 32, a cover 34, a frame 36, a first light source unit 38, a second light source unit 40, a third light source unit 42, a fourth light source unit 44, a fifth light source unit 46, and a diffuser plate 48.

The transmissive reflector plate 32 is formed of a light transmitting material, has an opening 3202 in the center, and assumes a dome shape, a radius of which is gradually expanded downward with a center axis 3204 of the opening 3202 set as the center.

The transmissive reflector plate 32 has a lower surface 3206 and an upper surface 3208 located on the opposite side of the lower surface 3206.

The lower surface 3206 is formed by a reflecting surface 32A on which fine unevenness for diffusing and reflecting light from below is formed.

The section of the opening 3202 of the transmissive reflector plate 32 is an erected section 3210 erected upward.

The cover 34 has an opening 3402 in the center and has an inner circumferential section 3404 made of an annular plane located around the opening 3402, an inclined section 3406 displaced downward from the outer end of the inner circumferential section 3404 toward the outside in the radial direction, and an outer circumferential section 3408 vertically provided in a cylindrical shape from the outer end of the inclined section 3406.

The cover 34 is arranged above the transmissive reflector plate 32 and forms a housing space S between the cover 34 and the transmissive reflector plate 32.

The lower surface of the cover 34 opposed to the transmissive reflector plate 32 is formed by a reflecting surface 34A.

The upper end of the erected section 3210 of the transmissive reflector plate 32 and the inner end of the inner circumferential section 3404 of the cover 34 are coupled.

The outer end on the outer side in the radial direction of the transmissive reflector plate 32 and the lower end of the outer circumferential section 3408 of the cover 34 are supported by a frame 36.

The frame 36 assumes an annular shape and holds the outer circumferential section of the transmissive reflector plate 32 and the outer circumferential section 3408 of the cover 34.

An annular plate section 3602 located below the outer circumferential section of the transmissive reflector plate 32 and extending along the outer circumferential section of the transmissive reflector plate 32 is provided in the frame 36.

The frame 36 is supported by the illumination-device-for-visual-inspection attaching section 2604 (FIG. 4).

The center axis 3204 of the opening 3202 and the optical axis L of the imaging optical system 1406 of the imaging apparatus 14 coincide with each other.

As shown in FIGS. 1 to 3, the first light source unit 38 includes plural light sources 3802 arranged in a first annular area 50 on the upper surface 3208 with the center axis 3204 set as the center.

In the first light source unit 38, lights emitted from the plural light sources 3802 are transmitted through the transmissive reflector plate 32 and cross an imaginary plane, which is orthogonal to the center axis 3204 and passes through the inspection object 2, at a first angle $\theta 1$ to illuminate the inspection object 2.

The imaginary plane passing through the inspection object 2 is a plane passing through the surface of the printed wiring board 402.

The plural light sources 3802 are supported by the cover 34 via a supporting member 3804 (FIG. 1).

As shown in FIGS. 1 to 3, the second light source unit 40 includes plural light sources 4002 arranged in a second annular area 52 on the upper surface 3208 having a radius larger than that of the first annular area 50 with the center axis 3204 set as the center.

In the second light source unit 40, lights emitted from the plural light sources 4002 are transmitted through the transmissive reflector plate 32 and cross the imaginary plane at a second angle $\theta 2$ smaller than the first angle $\theta 1$ to illuminate the inspection object 2.

The plural light sources 4002 are supported by the cover 34 via a supporting member 4004.

As shown in FIGS. 1 to 3, the third light source unit 42 includes plural light sources 4202 arranged in a third annular area 54 on the upper surface 3208 located between the first annular area 50 and the second annular area 52 with the center axis 3204 set as the center.

In the third light source unit 42, lights emitted from the plural light sources 4202 are transmitted through the transmissive reflector plate 32 and cross the imaginary plane at a third angle $\theta 3$ between the first angle $\theta 1$ and the second angle $\theta 2$ to illuminate the inspection object 2.

The third annular area 54 is divided into plural lighting areas 54A, 54B, 54C, and the like in the circumferential direction.

The third light source unit 42 is selectively turned on by the driving unit 20 for each of the plural light sources 4202 located in the lighting areas 54A, 54B, 54C, and the like.

The plural light sources 4202 are supported by the cover 34 via a supporting member 4204.

As shown in FIGS. 1 to 3, the fourth light source unit 44 includes plural light sources 4402 arranged along a lower section of the outer circumference of the transmissive reflector plate 32.

In the fourth light source unit 44, lights emitted from the plural light sources 4402 are diffused and reflected on the lower surface of the transmissive reflector plate 32 to illuminate the inspection object 2.

The plural light sources 4402 are supported by an annular plate section 3602.

As shown in FIGS. 1 and 2, the semi-transmissive diffuser plate 48 extending in an annular shape with the center axis 3204 set as the center is provided below the fourth light source unit 44, in this embodiment, below the annular plate section 3602.

The diffuser plate 48 has a front surface 4802 opposed to the inspection object 2 and a rear surface 4804 located on the opposite side of the front surface 4802.

The fifth light source unit 46 is arranged on the rear surface 4804. Therefore, as shown in FIG. 3, the fifth light source unit 46 is arranged in an annular area 56 with the center axis 3204 set as the center.

The fifth light source unit 46 includes plural light sources 4602 arranged in the annular area 56.

The annular area 56 is divided into plural lighting areas 56A, 56B, 56C, and the like in the circumferential direction.

The diffuser plate 48 is supported via the frame 36. The plural light sources 4602 are supported by the frame 36 via a not-shown supporting member.

In the fifth light source unit 46, lights emitted from the plural light sources 4602 are transmitted through the diffuser plate 48 and cross the imaginary plane at a fourth angle θ4 larger than the third angle θ3 to illuminate the inspection object 2.

The fifth light source unit 46 is selectively turned on by the driving unit 20 for each of the plural light sources 4602 located in the lighting areas 56A, 56B, 56C, and the like.

The operation of the visual inspection performed by using the illumination device for visual inspection 16 is explained below.

First, in the following explanation, as shown in FIG. 5, the inspection object 2 is the printed wiring board 402 applied with the cream solder 404.

It is assumed that the inspection object 2 is placed on the placing surface 30 in advance.

A driving current is supplied from the driving unit 20 to the first light source unit 38 according to the control by the control unit 22, whereby only the first light source unit 38 is turned on.

Then, lights emitted from the plural light sources 3802 of the first light source unit 38 are transmitted through the transmissive reflector plate 32 and cross the imaginary plane, which is orthogonal to the center axis 3204 and passes through the inspection object 2, at the first angle θ1 to illuminate the inspection object 2.

In this state, the imaging apparatus 14 performs imaging and the image processing unit 18 generates two-dimensional image data D1 of the inspection object 2.

Subsequently, the first light source unit 38 is turned off and a driving current is supplied from the driving unit 20 to the second light source unit 40 according to the control by the control unit 22, whereby only the second light source unit 40 is turned on.

Then, lights emitted from the plural light sources 4002 of the second light source unit 40 are transmitted through the transmissive reflector plate 32 and cross the imaginary plane, which is orthogonal to the center axis 3204 and passes through the inspection object 2, at the second angle θ2 to illuminate the inspection object 2.

In this state, the imaging apparatus 14 performs imaging and the image processing unit 18 generates two-dimensional image data D2 of the inspection object 2.

The lights emitted from the first and second light source units 38 and 40 are transmitted through the transmissive reflector plate 32 to be diffused to some extent and changes to generally parallel rays to illuminate the inspection object 2.

A part of the lights emitted from the first and second light source units 38 and 40 is reflected on the upper surface 3208 of the transmissive reflector plate 32. The reflected light is reflected again on the reflecting surface 34A of the cover 34 toward the transmissive reflector plate 32 and transmitted through the transmissive reflector plate 32 to illuminate the inspection object 2. This is advantageous in securing a light amount of light that illuminates the inspection object 2.

When the two two-dimensional image data D1 and D2 obtained by changing an angle of light irradiated on the inspection object 2 are obtained in this way, the control unit 22 calculates a difference between the two two-dimensional image data D1 and D2 to thereby obtain a contour of an image of the surface of the inspection object 2.

More specifically, a contour of the positioning mark 430, a contour of the pads 412, and a contour of the cream solder 404 are accurately obtained.

Therefore, the control unit 22 specifies the positions of the pads 412 with reference to the position of the positioning mark 430. The control unit 22 determines whether the position of the contour of the cream solder 404 with respect to the specified contour of the pads 412 or an area of the contour of the cream solder 404 satisfies inspection criteria set in advance and supplies a determination result to the not-shown external apparatus.

A reason for using the two two-dimensional image data D1 and D2 obtained by changing the angle of light irradiated on the inspection object 2 to the first angle θ1 and the second angle θ2 is explained below.

When the light is irradiated at the first angle θ1, since a difference between amounts of lights reflected by the cream solder 404 and the resist 420 is small, the two-dimensional image data D1 with relatively low contrast between the cream solder 404 and the resist 420 is obtained.

On the other hand, when the light is irradiated at the second angle θ2 smaller than the first angle θ1, since a difference between amounts of lights reflected by the cream solder 404 and the resist 420 is large, the two-dimensional image data D2 with relatively high contrast between the cream solder 404 and the resist 420 is obtained.

Calculating a difference between the two two-dimensional image data D1 and D2 having such a difference in contrast is advantageous in clearly obtaining a contour of an image of the surface of the inspection object 2.

The same principle holds when a chip component mounted on the cream solder 404 is inspected. Specifically, calculating a difference between the two two-dimensional image data D1 and D2 is advantageous in clearly obtaining a contour of an image of the chip component mounted on the surface of the printed wiring board 402.

Further, in order to obtain a more accurate contour of an image of the surface of the inspection object 2 generated by image processing by the control unit 22, it is desirable to further increase the contrast of an image of the inspection object 2 imaged by the imaging apparatus 14.

When the resist 420 applied over the surface of the inspection object 2 is green, if red is used as a color of light irradiated on the surface of the inspection object 2, the section of the resist 420 is imaged darker and the section of the pads 412 formed by copper foil is imaged brighter. Similarly, the resist section 436 of the positioning mark 430 is imaged darker and the copper foil section 438 is imaged brighter.

Therefore, using red as a color of lights irradiated from the first light source unit 38 and the second light source unit 42 is desirable in securing larger contrast.

A driving current is supplied from the driving unit 20 to the third light source unit 42 according to the control by the control unit 22, whereby only the third light source unit 42 is turned on.

Specifically, the third light source unit 42 is selectively turned on by driving unit 20 for each of the plural light sources 4202 located in the lighting areas 54A, 54B, 54C, and the like.

Then, lights emitted from the plural light sources 4202 of the third light source unit 42 are transmitted through the transmissive reflector plate 32 and cross the imaginary plane, which is orthogonal to the center axis 3204 and passes through the inspection object 2, at the third angle θ3 to illuminate the inspection object 2.

Every time the plural light sources 4202 located in the lighting areas 54A, 54B, 54C, and the like are selectively turned on, the imaging apparatus 14 performs imaging and the image processing unit 18 generates two-dimensional image data D3 of the inspection object 2.

The plural two-dimensional image data D3 are combined by using a publicly-known method in the past, for example, the photometric stereo method, whereby three-dimensional image data D4 is generated. In other words, the three-dimensional image data D4 having a component in the height direction of the inspection object 2 is generated and a stereoscopic shape of the inspection object 2 is obtained.

However, a shadow is formed in the inspection object 2 because the plural light sources 4202 located in the lighting areas 54A, 54B, 54C, and the like are selectively turned on. An image including the shadow is generated as the two-dimensional image data D3.

Therefore, the three-dimensional image data D4 generated on the basis of the two-dimensional image data D3 including the shadow includes an error.

Figure 6A:
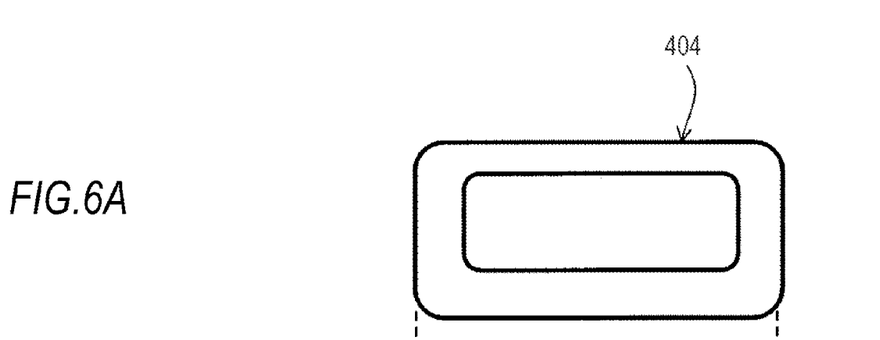
FIG. 6A is a plan view of the cream solder 404.
Figure 6B:
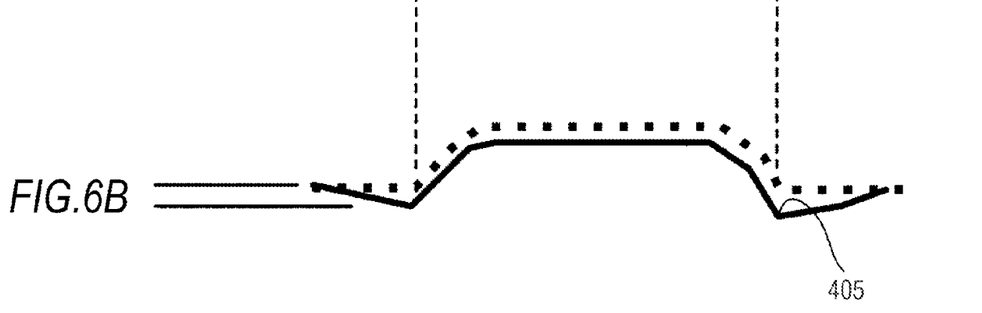
FIG. 6B is a side view of the cream solder 404.

Specifically, it is assumed that an actual stereoscopic shape of the cream solder 404 is as indicated by a broken line in FIGS. 6A and 6B. The three-dimensional image data D4 generated on the basis of the two-dimensional image data D3 including the shadow looks as if a recess 405 is formed around the cream solder 404 as indicated by a solid line.

A driving current is supplied from the driving unit 20 to the fourth light source unit 44 according to the control by the control unit 22, whereby only the fourth light source unit 44 is turned on.

Then, lights emitted from the plural light sources 4402 of the fourth light source unit 44 are diffused and reflected on the lower surface of the transmissive reflector plate 32 to illuminate the inspection object 2.

Since the lights diffused and reflected on the lower surface of the transmissive reflector plate 32 illuminate the inspection object 2 from the entire circumference of the inspection object 2, a shadow is not formed in the inspection object 2.

In this state, the imaging apparatus 14 performs imaging and the image processing unit 18 generates two-dimensional image data D5 of the inspection object 2.

The control unit 22 corrects the three-dimensional image data D4 using the two-dimensional image data D5 not including a shadow to thereby obtain accurate three-dimensional image data D6 of the inspection object 2 (the cream solder 404) indicated by a solid line in FIG. 6B.

Subsequently, the control unit 22 determines whether a stereoscopic shape of the inspection object 2 satisfies the inspection criteria set in advance and supplies a determination result to the not-shown external apparatus.

Specifically, the control unit 22 determines whether an amount of the cream solder 404 is too small or too large or the cream solder 404 is unevenly distributed (a blur of printing occurs) and supplies a determination result to the not-shown external apparatus.

Depending on the height of the inspection object 2, when imaging is performed in a state in which light emitted from the third light source unit 42 crosses the imaginary plane at the third angle θ3 to illuminate the inspection object 2, two-dimensional image data having information sufficient for generating three-dimensional image data is not obtained.

In that case, the inspection object 2 is illuminated by using the fifth light source unit 46 instead of the third light source unit 42.

Specifically, a driving current is supplied from the driving unit 20 to the fifth light source unit 46 according to the control by the control unit 22, whereby only the fifth light source unit 46 is turned on.

The fifth light source unit 46 is selectively turned on by the driving unit 20 for each of the plural light sources 4602 located in the lighting areas 56A, 56B, 56C, and the like.

Then, lights emitted from the plural light sources 4602 of the fifth light source unit 46 are transmitted through the diffuser plate 48 and cross the imaginary plane, which is orthogonal to the center axis 3204 and passes through the inspection object 2, at the fourth angle θ4 to illuminate the inspection object 2.

Every time the plural light sources 4602 located in the lighting areas 56A, 56B, 56C, and the like are selectively turned on, the imaging apparatus 14 performs imaging and the image processing unit 18 generates the two-dimensional image data D3 of the inspection object 2.

Thereafter, the same operation is performed.

For accurately imaging a surface shape of the inspection object 2 with the imaging apparatus 14, lights emitted from the third light source unit 42 and the fifth light source unit 46 are desirably lights having a short wavelength component. Specifically, blue light is desirable or white light including a blue wavelength component is desirable.

This is because, as a wavelength component of light is shorter, the light is less easily affected by diffraction.

For accurately discriminating a color of the inspection object 2 with the imaging apparatus 14, light emitted from the fourth light source unit 44 is desirably white light.

This is because the discrimination of the color of the inspection object 2 makes it easy to distinguish the inspection object 2 from a section other than the inspection object 2.

According to this embodiment, since the first, second, third, and fourth light source units 38, 40, 42, and 44 are selected and used, it is possible to cope with plural kinds of visual inspection performed by using a three-dimensional image and a two-dimensional image.

Therefore, unlike the past, it is unnecessary to separately prepare an illumination device for visual inspection for a three-dimensional image and an illumination device for visual inspection for a two-dimensional image. This is advantageous in reducing labor and time and cost necessary for visual inspection.

The present application contains subject matter related to that disclosed in Japanese Priority Patent Application JP 2009-085257 filed in the Japan Patent Office on Mar. 31, 2009, the entire contents of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An illumination device for visual inspection comprising:
   a transmissive reflector plate that is formed of a light transmitting material, has an opening in a center, assumes a dome shape having a radius that is gradually expanded downward with a center axis of the opening set as a center, and has a lower surface formed of a reflecting surface on which is formed fine unevenness for diffusing and reflecting light from below and an upper surface located on an opposite side of the lower surface;
   first, second, and third light source units to irradiate light on an inspection object, the first, second, and third light source units being provided on an upper surface side of the transmissive reflector plate and arranged in a place below the opening and passing the center axis; and
   a fourth light source unit to irradiate light on the inspection object, the fourth light source unit being provided below the transmissive reflector plate, wherein
   the first light source unit includes first multiple light sources arranged in a first annular area on the upper surface with the center axis set as a center, wherein light emitted from the first multiple light sources is transmitted through the transmissive reflector plate and crosses an imaginary plane, the imaginary plane being is orthogonal to the center axis and passing through the inspection object, at a first angle to illuminate the inspection object,
   the second light source unit includes second multiple light sources arranged in a second annular area on the upper surface having a radius larger than that of the first annular area with the center axis set as a center, wherein light emitted from the second multiple light sources is transmitted through the transmissive reflector plate and crosses the imaginary plane at a second angle smaller than the first angle to illuminate the inspection object,
   the third light source unit includes third multiple light sources arranged in a third annular area on the upper surface located between the first annular area and the second annular area with the center axis set as a center, wherein light emitted from the third multiple light sources is transmitted through the transmissive reflector plate and crosses the imaginary plane at a third angle between the first angle and the second angle to illuminate the inspection object, and
   the fourth light source unit includes fourth multiple light sources arranged along a lower part of an outer circumference of the transmissive reflector plate, wherein light emitted from the plural light sources is diffused and reflected by the lower surface of the transmissive reflector plate to illuminate the inspection object.

2. The illumination device for visual inspection according to claim 1, wherein
   a cover that forms a housing space between the cover and the transmissive reflector plate is provided above the transmissive reflector plate, and
   the first, second, and third light source units are supported by the cover and housed in the housing space.

3. The illumination device for visual inspection according to claim 2, wherein a cover lower surface of the cover opposed to the transmissive reflector plate is formed by a cover reflecting surface.

4. The illumination device for visual inspection according to claim 1, wherein
   a cover that forms a housing space between the cover and the transmissive reflector plate is provided above the transmissive reflector plate,
   an annular frame that holds an outer circumference of the transmissive reflector plate and an outer circumference of the cover is provided,
   an annular plate section located below the outer circumference of the transmissive reflector plate and extending along the outer circumference of the transmissive reflector plate is provided in the annular frame, and
   the fourth light source unit is supported by the annular plate section.

5. The illumination device for visual inspection according to claim 1, wherein
   a semi-transmissive diffuser plate extending in an annular shape with the center axis set as a center is provided below the fourth light source unit,
   the diffuser plate has a front surface opposed to the inspection object and a rear surface located on an opposite side of the front surface,
   a fifth light source unit is arranged on the rear surface, and
   light emitted from the fifth light source unit is transmitted through the diffuser plate and crosses the imaginary plane at a fourth angle smaller than the second angle to illuminate the inspection object.

6. The illumination device for visual inspection according to claim 5, wherein
   the fifth light source unit is arranged in a fifth annular area with the center axis set as a center,
   the fifth annular area is divided into fifth multiple lighting areas in a circumferential direction,
   the fifth light source unit includes fifth multiple light sources arranged in the fifth annular area, and
   the fifth light source unit is selectively turned on for each of the fifth multiple light sources located in the respective lighting areas.

7. The illumination device for visual inspection according to claim 1, wherein
   the third annular area is divided into third multiple lighting areas in a circumferential direction, and
   the third light source unit is selectively turned on for the each of the third multiple light sources located in the respective lighting areas.

8. A visual inspection apparatus comprising:
   a base including a base body on which an inspection object is placed and a column erected from the base body;
   an imaging apparatus supported by the column with an optical axis of an imaging optical system thereof directed downward;
   a transmissive reflector plate that is supported by the column and formed of a light transmitting material, has an opening in a center through which the imaging apparatus is inserted from above, assumes a dome shape having a radius that is gradually expanded downward with a center axis of the opening set as a center, and has a lower surface formed of a reflecting surface on which is formed fine unevenness for diffusing and reflecting light from below and an upper surface located on an opposite side of the lower surface;
   first, second, and third light source units to irradiate light on an inspection object, the first, second, and third light source units being provided on an upper surface side of the transmissive reflector plate and arranged in a place below the opening and passing the center axis; and a fourth light source unit to irradiate light on the inspection object, the fourth light source unit being provided below the transmissive reflector plate, wherein the first light source unit includes first multiple light sources arranged in an first annular area on the upper surface with the center axis set as a center, wherein light emitted from the first multiple light sources is transmitted through the transmissive reflector plate and crosses an imaginary plane, the imaginary plane being orthogonal to the center axis and passing through the inspection object, at a first angle to illuminate the inspection object, the second light source unit includes second multiple light sources arranged in a second annular area on the upper surface having a radius larger than that of the first annular area with the center axis set as a center, wherein light emitted from the plural second multiple light sources is transmitted through the transmissive reflector plate and crosses the imaginary plane at a second angle smaller than the first angle to illuminate the inspection object, the third light source unit includes third multiple light sources arranged in a third annular area on the upper surface located between the first annular area and the second annular area with the center axis set as a center, wherein light emitted from the third multiple light sources is transmitted through the transmissive reflector plate and crosses the imaginary plane at a third angle between the first angle and the second angle to illuminate the inspection object, and the fourth light source unit includes fourth multiple light sources arranged along a lower part of an outer circumference of the transmissive reflector plate, wherein light emitted from the fourth multiple light sources is diffused and reflected by the lower surface of the transmissive reflector plate to illuminate the inspection object.

* * * * *